(12) United States Patent
Chu et al.

(10) Patent No.: US 10,106,550 B2
(45) Date of Patent: Oct. 23, 2018

(54) AZA-PHENALENE-3-KETONE DERIVATIVE, PREPARATION METHOD THEREOF, AND ITS APPLICATION AS PARP INHIBITOR

(71) Applicant: SUZHOU KANGRUN PHARMACEUTICALS INC., Wujiang (CN)

(72) Inventors: Yuping Chu, Wujiang (CN); Weiliang Xu, Wujiang (CN); Ling Wang, Wujiang (CN); Weizheng Xu, Wujiang (CN)

(73) Assignee: SUZHOU KANGRUN PHARMACEUTICALS INC., Wujiang (CN)

( * ) Notice: Subject to any disclaimer, the term of this patent is extended or adjusted under 35 U.S.C. 154(b) by 0 days.

(21) Appl. No.: 15/572,838

(22) PCT Filed: May 4, 2016

(86) PCT No.: PCT/CN2016/081035
§ 371 (c)(1),
(2) Date: Nov. 9, 2017

(87) PCT Pub. No.: WO2016/188307
PCT Pub. Date: Dec. 1, 2016

(65) Prior Publication Data
US 2018/0134722 A1    May 17, 2018

(30) Foreign Application Priority Data
May 25, 2015  (CN) .......................... 2015 1 0267732

(51) Int. Cl.
*C07D 487/16*  (2006.01)
(52) U.S. Cl.
CPC ................. *C07D 487/16* (2013.01)

(58) Field of Classification Search
CPC .................................................. C07D 401/06
See application file for complete search history.

(56) References Cited

U.S. PATENT DOCUMENTS 6,291,425 B1    9/2001  Li et al.

FOREIGN PATENT DOCUMENTS

| CN | 1805964 | A | 7/2006 |
|---|---|---|---|
| CN | 101223175 | A | 7/2008 |
| CN | 102083314 | A | 6/2011 |
| CN | 102869258 | A | 1/2013 |
| CN | 103936735 | A | 7/2014 |
| CN | 104169283 | A | 11/2014 |
| CN | 104945406 | A | 9/2015 |
| WO | 2004105700 | A2 | 12/2004 |

*Primary Examiner* — Paul V Ward
(74) *Attorney, Agent, or Firm* — SZDC Law P.C.; Feng Shan

(57) ABSTRACT

Disclosed are an aza-phenalene-3-ketone derivative, a preparation method thereof and its application as a PARP inhibitor. The aza-phenalene-3-ketone derivative has the following structure:

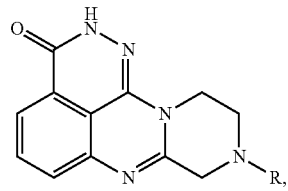

wherein R is hydrogen, methyl, ethyl, isopropyl, benzyl or 3-methyl-3-butenyl. The aza-phenalene-3-ketone derivative has very high activity for inhibiting PARP, thereby providing a good basis for new drug research of developing a nitrogen-doped phenalene-3-ketone compound as PARP inhibitor to treat cancer.

5 Claims, 1 Drawing Sheet

AZA-PHENALENE-3-KETONE DERIVATIVE, PREPARATION METHOD THEREOF, AND ITS APPLICATION AS PARP INHIBITOR

This application is a national stage application of PCT/CN2016/081035, filed on May 4, 2016, which claims priority to Chinese Patent Application No. 201510267732.1, filed on May 25, 2015, which is incorporated by reference for all purposes as if fully set forth herein.

FIELD OF THE INVENTION

The present invention relates to the field of pharmaceutical synthesis, and in particular, to an aza-phenalene-3-ketone derivative and its application as a PARP inhibitor.

BACKGROUND OF THE INVENTION

Poly(adenosinediphosphate-ribose)-polymerase or poly(ADP-ribose)-polymerase (PARP) exists in mammalian cells and most eukaryotic cells, and is a class of catalyzed polyglutase diphosphate ribosylated ribozyme. PARP is closely related to many physiological processes, including chromosomal stabilization, DNA damage identification and repair, gene transcription, and cell apoptosis and necrosis. After its discovery, the important role of PARP in DNA damage repair and maintenance of genome stability has attracted wide attention. In all types of DNA damage, DNA single-stranded lesions occur most frequently, and the enzyme involved in a series of repair pathways is PARP. PARP detects DNA breaks, and is activated after DNA damage and binds to DNA breaks through an N-terminal DBD (Dibenzamido Diphenyl Disulfide) containing two zinc fingers, increasing the catalytic activity by 10-500 times.

Conventional chemotherapy and radiotherapy directly or indirectly attack DNA, causing DNA damage to tumor cells and killing the cancer cells. In tumor cells, however, DNA repair enzyme is overexpressed, and DNA damage self-repair mechanism is activated, thereby generating chemotherapy and radiotherapy resistant. Research has shown that PARP inhibitor can block the DNA repair pathway, reducing the ability of tumor cells to repair itself, so the PARP inhibitor in combination with chemotherapy can effectively enhance the anti-tumor effect. Research also found that PARP inhibitor monotherapy effectively inhibits BRCA1/2 (breast cancer type susceptibility protein) gene deletion or mutation in breast cancer and ovarian cancer.

In summary, PARP inhibitor has broad application in antitumor research and therapy. Therefore, the present invention is intended on the basis of preliminary studies, to design and synthesize a new series of aza-phenalene-3-ketone derivatives. The activities of the derivatives have been screened and studies, and the derivatives can be used in anti-tumor drug research.

SUMMARY OF THE INVENTION

An objective of the present invention is to solve the deficiencies of the existing technology, and to provide an aza-phenalene-3-ketone derivative and its application as a PARP inhibitor, its preparation method and its application as a PARP inhibitor. The aza-phenalene-3-ketone derivative of the present invention has high inhibitory activity against PARP, and can be used as PARP inhibitor in anti-tumor drug research.

An aza-phenalene-3-ketone derivative has the following Formula (I):

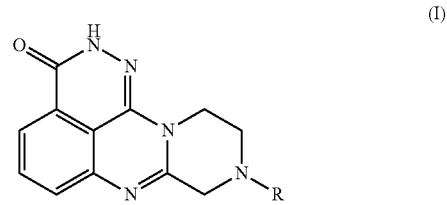

In Formula (I), R is H, methyl, ethyl, isopropyl, benzyl, or 3-methyl-3-butenyl.

The synthetic route to prepare the aza-phenalene-3-ketone derivative is as follows:

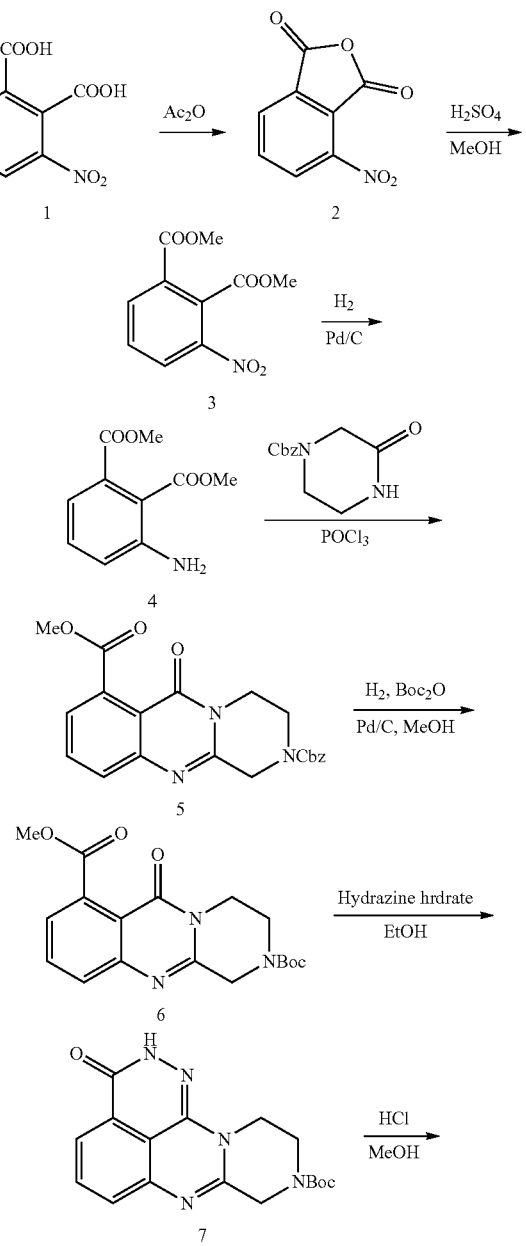

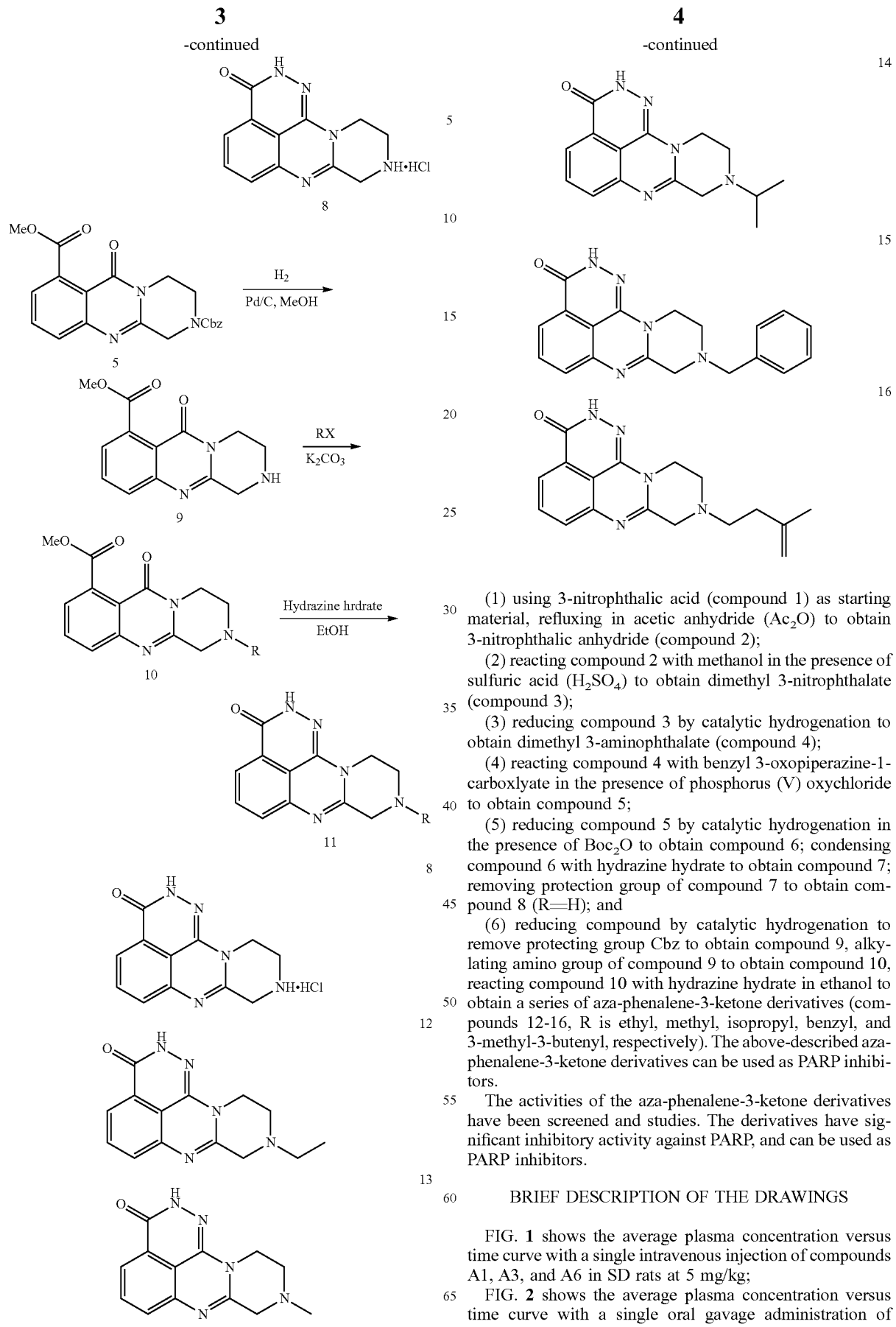

(1) using 3-nitrophthalic acid (compound 1) as starting material, refluxing in acetic anhydride (Ac$_2$O) to obtain 3-nitrophthalic anhydride (compound 2);

(2) reacting compound 2 with methanol in the presence of sulfuric acid (H$_2$SO$_4$) to obtain dimethyl 3-nitrophthalate (compound 3);

(3) reducing compound 3 by catalytic hydrogenation to obtain dimethyl 3-aminophthalate (compound 4);

(4) reacting compound 4 with benzyl 3-oxopiperazine-1-carboxlyate in the presence of phosphorus (V) oxychloride to obtain compound 5;

(5) reducing compound 5 by catalytic hydrogenation in the presence of Boc$_2$O to obtain compound 6; condensing compound 6 with hydrazine hydrate to obtain compound 7; removing protection group of compound 7 to obtain compound 8 (R=H); and (6) reducing compound by catalytic hydrogenation to remove protecting group Cbz to obtain compound 9, alkylating amino group of compound 9 to obtain compound 10, reacting compound 10 with hydrazine hydrate in ethanol to obtain a series of aza-phenalene-3-ketone derivatives (compounds 12-16, R is ethyl, methyl, isopropyl, benzyl, and 3-methyl-3-butenyl, respectively). The above-described aza-phenalene-3-ketone derivatives can be used as PARP inhibitors.

The activities of the aza-phenalene-3-ketone derivatives have been screened and studies. The derivatives have significant inhibitory activity against PARP, and can be used as PARP inhibitors.

DETAILED DESCRIPTION OF THE ILLUSTRATED EMBODIMENTS

Figure 1:
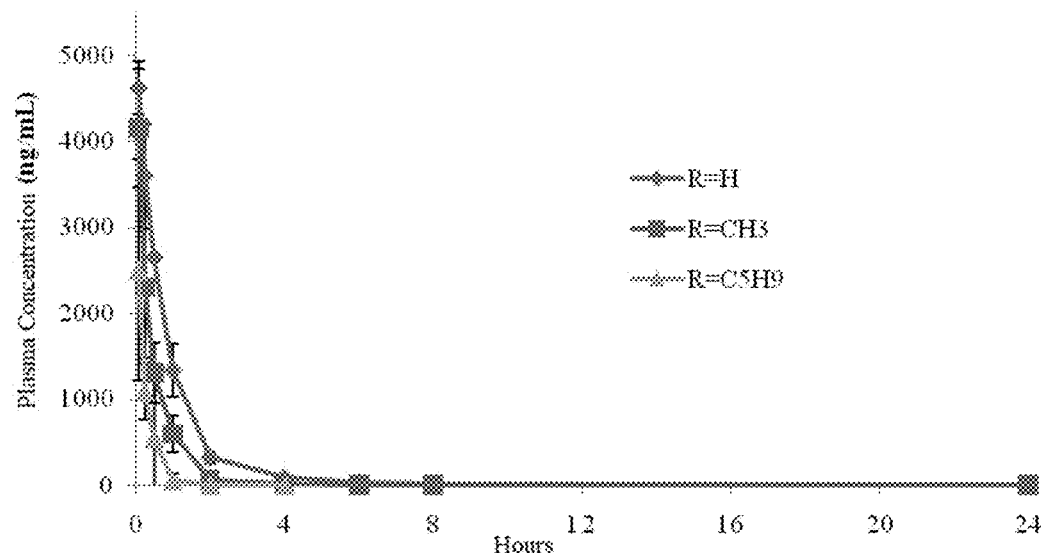
FIG. 1 shows the average plasma concentration versus time curve with a single intravenous injection of compounds A1, A3, and A6 in SD rats at 5 mg/kg.

Reference will now be made in detail to embodiments of the present invention.

Example 1 Synthesis of aza-phenalene-3-ketone derivatives (1) Synthesis of 3-nitrophthalic anhydride (compound 2)

3-nitrophthalic acid (48.5 g, 0.23 mol) was mixed with acetic anhydride (45 mL), and the resulting mixture was stirred at reflux for 1 hour. After completion of the reaction, the mixture was cooled to 80° C., 100 mL of methyl tert-butyl ether was added to the mixture, and the mixture was continued to stir until cooled to 15° C. The mixture was filtered, and the resulted solid was washed with methyl tert-butyl ether and dried at 40° C. to give compound 2 as a white product (36.7 g, 82%).

(2) Synthesis of dimethyl 3-nitrophthalate (compound 3)

3-Nitrophthalic anhydride (15 g, 77.7 mmol) from step (1) was dissolved in 200 mL of methanol and 5 mL of concentrated sulfuric acid was added. The mixture was heated to reflux for 16 hours. After cooled to room temperature, the reaction mixture was poured into ice water. The mixture was then filtered, and the resulted solid was washed with water and dried to give compound 3 (13.1 g, 71%).

(3) Synthesis of dimethyl 3-aminophthalate (compound 4)

Dimethyl 3-nitrophthalate (18.1 g, 75.7 mmol) from step (2) was dissolved in 400 mL ethanol and 10% Pd/C (50% water, 1.8 g) was added. The reaction mixture was stirred overnight under a hydrogen atmosphere. The reaction mixture was filtered, and the filter cake was wash with ethanol. Ethanol was removed to give compound 4 as a yellow solid (14.2 g, 90%).

(4) Synthesis of Compound 5

Dimethyl 3-aminophthalate (compound 4) (8.3 g, 40 mmol), benzyl 3-oxopiperazine-1-carboxlyate (10.31 g, 44 mmol), and phosphorus oxychloride (12.27 g, 7.3 mL) were successively added 1,4-dioxane (280 mL). The resulted reaction mixture was stirred at 80° C. for 2 hour. The mixture was concentrated to give an oily crude product, which was purified by column chromatography to give compound 5 (14.6 g, 93%).

(5) Synthesis of Compound 6

Compound 5 (3.93 g, 10 mmol), Boc$_2$O (di-tert-butyl dicarbonate) (2.4 g, 11 mmol), and 10% Pd/C (50% water, 0.4 g) were added to methanol (280 mL) and stirred overnight under a hydrogen atmosphere. The reaction mixture was filtered, and the filter cake was washed with methanol. Methanol was removed to give a crude product, which was purified by column chromatography to give compound 6 as a yellow oily product compound 6 (3.52 g, 98%).

(6) Synthesis of Compound 7

Compound 6 (1.9 g, 5.3 mmol) was added to 10 mL of absolute ethanol, and hydrazine monohydrate (85%, 4 mL) was then added. The reaction mixture was stirred at reflux until completion. After reaction mixture was cooled to room temperature, water (20 mL) and ethyl acetate (20 mL) were added and stirred for 5 minutes. The organic layer was separated, and ethyl acetate was removed to give a crude product. The crude product was purified by column chromatography to give compound 7 as an off-white solid (0.20 g, 11%).

(7) Synthesis of Compound 8

Compound 7 (0.20 g, 0.6 mmol) was added to a methanol solution of hydrogen chloride (4 M, 10 mL), and the reaction mixture was stirred for 4 hours at room temperature. The mixture was concentrated to give compound 8 as an off-white solid (0.15 g, 92%).

$^1$H NMR (400 MHz, DMSO-d6): δ=12.08 (s, 1H), 7.82-7.94 (m, 2H), 7.63 (d, J=8.0 Hz, 1H), 3.63-4.25 (m, 6H).

(8) Synthesis of Compound 12

Compound 5 (6.0 g, 15.2 mmol) and 10% Pd/C (50% water, 0.6 g) in methanol (80 mL) were stirred overnight under a hydrogen atmosphere. The reaction mixture was filtered and washed with methanol. Methanol was removed to give a crude produce. The crude product was purified by column chromatography to give compound 9 as a yellow oily product (2.8 g, 71%).

Compound 9 (1.48 g, 5.7 mmol), potassium carbonate (1.57 g, 11.4 mmol), ethyl iodide (1.78 g, 11.4 mmol), and acetonitrile (30 mL) were stirred at room temperature overnight. The mixture was filtered and the filtrate was concentrated to give a crude product. The crude product was purified by column chromatography to give a yellow-white solid (1.10 g, 67%).

The yellow-white product (1.9 g, 5.3 mmol) was added to 20 mL of absolute ethanol, and hydrazine monohydrate (85%, 4 mL) was then added. The reaction mixture was stirred at reflux until completion. After the reaction mixture was cooled to room temperature, water (20 mL) and ethyl acetate (20 mL) were added, and the mixture was stirred for 5 minutes. The organic layer was separated, and ethyl acetate was removed to give a crude product. After the crude product was purified by column chromatography to give an off-white solid product Compound 12 (0.20 g, 14.6%).

$^1$H NMR (400 MHz, CDCl$^3$): δ=9.71 (s, 1H), 7.99 (m, J=8.0 Hz, 1H), 7.82 (m, 1H), 7.60 (d, J=8.0 Hz, 1H), 3.83 (m, 2H), 3.64 (s, 2H), 2.94 (m, 2H), 2.63 (m, 2H), 1.22 (t, J=7.2 Hz, 3H).

(9) Synthesis of Compound 13

Compound 9 (1.70 g, 6.5 mmol), aqueous formaldehyde (37%, 6 mL), sodium cyanoborohydride (4.24 g, 20 mmol), acetic acid (0.5 mL) and acetonitrile (30 mL) were stirred at room temperature for 1.5 hours. The mixture was filtered and concentrated to give a crude product. The crude product was purified by column chromatography to give a yellow-white solid (1.32 g, 74%).

The yellow-white product (1.25 g, 4.57 mmol) was added to 20 mL of absolute ethanol, and hydrazine monohydrate (85%, 4 mL) was then added. The reaction mixture was stirred at reflux until completion. After the reaction mixture was cooled to room temperature, water (20 mL) and ethyl acetate (20 mL) were added and stirred for 5 minutes. The organic layer was separated, and ethyl acetate was removed. The crude product was purified by column chromatography to give compound 13 as an off-white solid product (0.18 g, 15.4%).

$^1$H NMR (400 MHz, DMSO-d6): δ=11.90 (s, 1H), 7.72-7.86 (m, 2H), 7.51-7.54 (m, 1H), 3.49-3.71 (m, 4H), 2.86 (t, J=5.6 Hz, 2H), 2.37 (s, 3H).

(10) Synthesis of Compound 14

Compound 9 (3.0 g, 11.57 mmol), potassium carbonate (2.07 g, 15 mmol), isopropyl bromide mixture of propane (8.54 g, 69.4 mmol) and DMF (30 mL) was stirred at 80° C. 5 hours. The mixture was filtered and the filtrate have spin dry after drying, the crude product was purified by column chromatography to give a yellow-white solid (1.84 g, 53%); the product (1.80 g, 5.97 mmol) was added 30 mL of anhydrous ethanol and then adding an aqueous hydrazine monohydrate (85%, 5 mL). The reaction mixture was stirred at reflux until completion. After the reaction mixture was cooled to room temperature, water was added (30 mL) and ethyl acetate (30 mL) and stirred for 5 minutes. The organic layer was separated and dried spin dry. After the crude product was purified by column chromatography to give white solid compound 14 (0.27 g, 15.9%).

(11) Synthesis of Compound 15

Compound 9 (1.29 g, 5 mmol), potassium carbonate (1.38 g, 10 mmol), benzyl chloride (0.83 g, 6.5 mmol) and acetonitrile (20 mL) were stirred for 5 hours at room temperature. The mixture was filtered and the filtrate was concentrated to give a crude product. The crude product was purified by column chromatography to give a yellow-white solid (1.25 g, 71.5%).

The yellow-white product (1.24 g, 3.55 mmol) was added to 20 mL of absolute ethanol, and hydrazine monohydrate (85%, 4 mL) was then added. The reaction mixture was stirred at reflux until completion. After the reaction mixture was cooled to room temperature, water (30 mL) and ethyl acetate (30 mL) were added and stirred for 5 minutes. The organic layer was separated and concentrated to give a crude product. After the crude product was purified by column chromatography to give compound 15 as a white solid (0.22 g, 18.7%).

$^1$H NMR (400 MHz, DMSO-d6): δ=11.92 (s, 1H), 7.71-7.84 (m, 2H), 7.31-7.49 (m, 6H), 3.70 (m, 4H), 3.52 (s, 2H), 2.91 (m, 2H).

(12) Synthesis of Compound 16

Compound 9 (4.0 g, 15.4 mmol), potassium carbonate (4.28 g, 31 mmol), 3-methyl-3-butenyl methanesulfonate (3.8 g, 23.1 mmol), and acetonitrile (40 mL) were stirred at 60° C. for 5 hours. The mixture was filtered and the filtrate was concentrated to give a crude product. The crude product was purified by column chromatography to give a yellow-white solid (3.12 g, 62%).

The yellow-white product (3.10 g, 9.47 mmol) was added to 50 mL of absolute ethanol, and hydrazine monohydrate (85%, 6 mL) was then added. The reaction mixture was stirred at reflux until completion. After the reaction mixture was cooled to room temperature, water (40 mL) and ethyl acetate (40 mL) were added and stirred for 5 minutes. The organic layer was separated and ethyl acetate was removed to give a crude product. After the crude product was purified by column chromatography to give compound 16 as a white solid (0.45 g, 15.4%).

$^1$H NMR (400 MHz, DMSO-d6): δ=11.88 (s, 1H), 7.71-7.85 (m, 2H), 7.52 (m, 1H), 4.76 (m, 2H), 3.57-3.69 (m, 4H), 2.94 (s, 2H), 2.62 (d, J=7.2 Hz, 2H), 2.28 (d, J=8.4 Hz, 2H), 1.75 (s, 3H).

Example 2 Activity of aza-phenalene-3-ketone derivatives

1. Measuring PARP1 Inhibitory Activity 1.1 Materials and Methods

Universal PARP colorimetric assay kit (US Trevigen company)

1.2 PARP1 Inhibitory Activity Test Results

| Compound | Structure | IC$_{50}$ (nM) |
|---|---|---|
| 3-AB Standard | 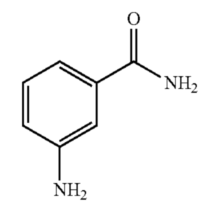 | 100% (inhibition rate, 1 mM) |
| BSI-201 Positive Control | 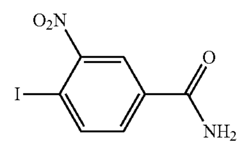 [SMILES: NC(=O)c1ccc(I)c([N+](=O)[O-])c1] | 22.4% (inhibition rate, 1 μM) |
| A1 | 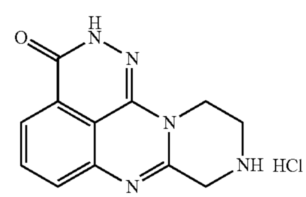 [SMILES: O=c1[nH]nc2c3c(cccc13)N=C1CNCCN12 ; Cl] | 90.5 |
| A2 | 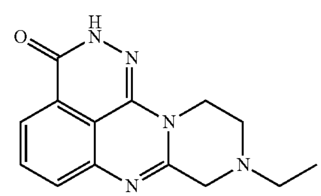 [SMILES: CCN1CCN2C(=Nc3cccc4c(=O)[nH]nc2c34)C1] | 65.7 |
| A3 | 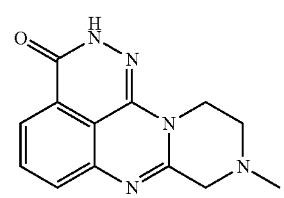 [SMILES: CN1CCN2C(=Nc3cccc4c(=O)[nH]nc2c34)C1] | 130 |
| A4 | 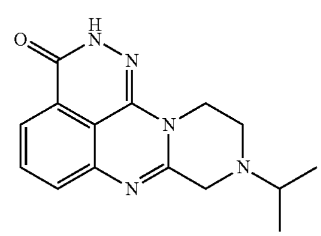 [SMILES: CC(C)N1CCN2C(=Nc3cccc4c(=O)[nH]nc2c34)C1] | 111 |

| Compound | Structure | IC$_{50}$ (nM) |
|---|---|---|
| A5 | 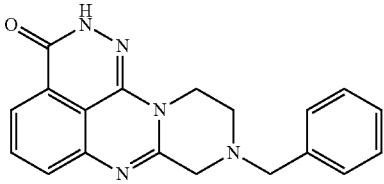 [SMILES: O=c1[nH]nc2c3c(cccc13)N=C1CN(Cc3ccccc3)CCN12] | 58.7 |

-continued

| Compound | Structure | IC$_{50}$ (nM) |
|---|---|---|
| A6 | 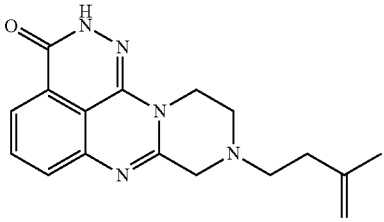 [SMILES: C=C(C)CCN1CCN2C(=Nc3cccc4c(=O)[nH]nc2c34)C1] | 39.1 |

2. Preliminary Pharmacokinetics Study of Compounds A1, A3, A6 in SD Rats

Considering compounds' PARP inhibition rates IC$_{50}$, there compounds A1, A3, and A6 (where: A1=compound 8; A2=compound 12; A3=compound 13; A4=compound 14; A5=compound 15; A6=compound 16) were selected for pharmacokinetic study.

2.1 Materials and Methods 2.1.1 Instruments

Agilent 1200 HPLC; API QTAP 4000 LC-MS/MS System 2.1.2 Test Animals

Healthy SPF SD male rats: 18, weighing 180-220 g, purchased from Shanghai Si Lai Ke Lab Animal Co. Ltd.; animal license no. SOCK (Shanghai) 2013-00016.

2.1.3 Experimental Procedure

Rats were divided into intravenous injection group and oral gavage administration group, and fast for 12-14 hours before experiments. Test compounds' concentration in venous blood was measured. Venous blood was collected by orbital, EDTAK2 anticoagulation. The blood samples were placed on ice, and centrifuged within 30 minutes to separate plasma (centrifugal condition: 5000 rpm/min, 10 min, room temperature). The samples were stored at −80° C. prior to analysis.

Rats in intravenous injection group received a single injection 5 mL/kg of the test compounds. Rats in oral gavage administration group received a single dose 10 mL/kg of the test compounds. Venous blood sample collection times were: before the injection of the test compound (0 hr); after the injection of the test compound: 15 min, 30 min, 1 h, 2 h, 4 h, 6 h, 8 h and 24 h; before the oral gavage administration of the test compound (0 hr) and after the oral gavage administration of the test compounds, 30 min, 1 h, 2 h, 4 h, 6 h, 8 h and 24 h.

2.1.4 the Measurement Conditions

Liquid phase conditions: column: Agilent Eclipse plus-C18 (4.6×150 mm, 5.0 μm), mobile phase: 0.1% aqueous formic acid (A)/0.1% formic acid in acetonitrile (B); gradient elution, flow rate: 1.00 mL/min (split v:v=1:1); injection volume: 10 μL.

MS conditions: using electrospray ionization (ESI) and the positive ion mode under multiple reaction monitoring (MRM).

| A1: m/z 242.30/187.30 | A3: m/z 255.90/0.30 | A3: m/z 310.00/254.40 | IS: m/z 455.30/165.10 |
|---|---|---|---|
| DP: 73 V | DP: 77 V | DP: 69 V | DP: 90 V |
| CE: 37 eV | CE: 45 eV | CE: 26 eV | CE: 37 eV |
| CXP: 11 V | CXP: 12 V | CXP: 5 V | CXP: 9 V |
| Gas 1: 60 psi | | Spray Voltage: 5000 V | |
| Gas 2: 40 psi | | Temprature: 500° C. | |
| Curtain Gas: 15 psi | | CAD: High | |

2.1.5 Standard Solution Preparation

Compounds A1, A3, and A6 were weighed precisely and added to MDSO to prepare 1.00 mg/mL stock solutions. After the stock solutions were diluted to prepare 10000, 5000, 2000, 1000, 500, 100, 50.0, 20.0 ng/mL standard working solutions. Quality control work concentrations include low (30 ng/mL), medium (500 ng/mL), and high (8000 ng/mL).

2.1.6 Plasma Sample Processing Method

10 μL plasma sample was added 100 μL verapamil internal standard solution. The mixture was vortexed for 60 seconds and then centrifuged (12000 rpm, 3 min). 70 μL supernatant was transferred to a 96-well plate with equal volume of water in each well. LC-MS/MS analysis was then conducted, and the injection volume was 10 μL.

2.1.7 Data Processing

Data were processed by using WinNonlin 6.3 pharmacokinetic calculation software and non-compartment pharmacokinetic model to obtain major pharmacokinetic parameters.

2.2 Method Validation

Based on-clinical pharmacokinetic study technical guidelines, SD rat plasma was subject to method validation in the followings: method specificity, standard curve linearity, precision and accuracy, limits of quantitation, plasma ten-fold dilution accuracy, matrix effect and extraction recovery, all meeting the requirements of biological sample analysis.

2.3 Pharmacokinetic Results

Figure 2:
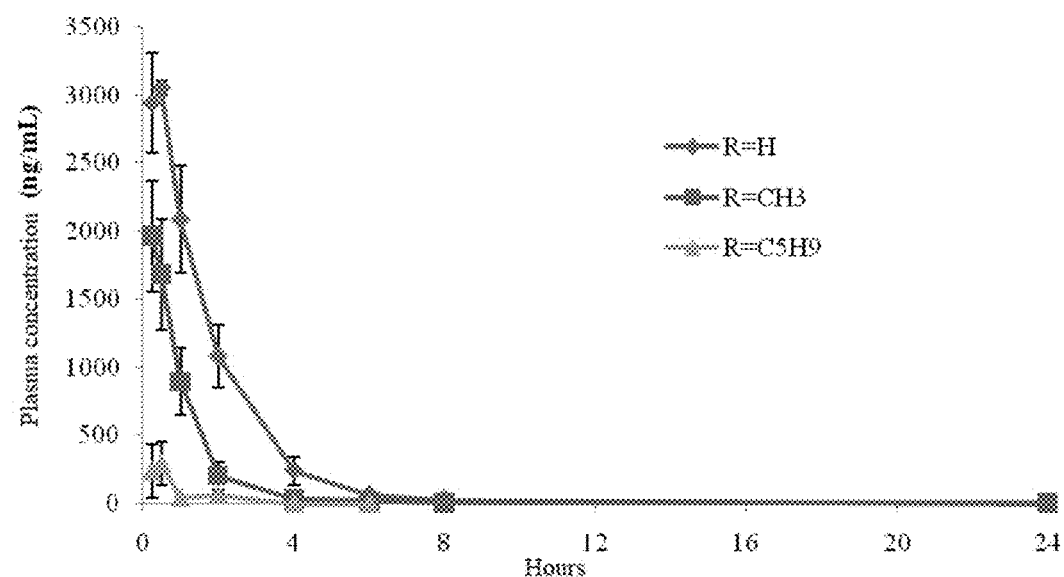
FIG. 2 shows the average plasma concentration versus time curve with a single oral gavage administration of compounds A1, A3, and A6 in SD rats at 10 mg/kg.

FIG. 1 shows the average plasma concentration versus time curve with a single intravenous injection of compounds A1, A3, and A6 in SD rats at 5 mg/kg; FIG. 2 shows the average plasma concentration versus time curve with a single oral gavage administration of compounds A1, A3, and A6 in SD rats at 10 mg/kg.

TABLE 1

SD Pharmacokinetic parameters of SD rats after a single intravenous injection of A1, A3, and A6 at 5 mg/kg

| Parameters | Units | Intravenous injection | | |
|---|---|---|---|---|
| | | A1 (R = H) Mean ± SD | A3 (R = CH$_3$) Mean ± SD | A6 (R = C$_5$H$_9$) Mean ± SD |
| Dosage | mg · kg$^{-1}$ | | 5.00 | |
| K$_{el}$ | h$^{-1}$ | 0.463 ± 0.063 | 1.02 ± 0.034 | 3.64 ± 0.22 |
| t$_{1/2}$ | h | 1.53 ± 0.16 | 0.722 ± 0.082 | 0.191 ± 0.012 |
| AUC$_{0-t}$ | h · ng · mL$^{-1}$ | 4252 ± 304 | 2286 ± 323 | 1004 ± 92 |
| AUC$_{0-inf}$ | h · ng · mL$^{-1}$ | 4281 ± 317 | 2290 ± 321 | 1038 ± 118 |
| AUMC$_{0-t}$ | h · h · ng · mL$^{-1}$ | 3790 ± 547 | 1145 ± 120 | 196 ± 27 |
| AUMC$_{0-inf}$ | h · h · ng · mL$^{-1}$ | 4190 ± 575 | 1175 ± 105 | 232 ± 17 |
| CL | mL · kg$^{-1}$ · min$^{-1}$ | 19.5 ± 1.4 | 38.4 ± 2.5 | 83.1 ± 13.3 |
| MRT$_{IV}$ | h | 0.953 ± 0.104 | 0.506 ± 0.040 | 0.222 ± 0.026 |
| Vd$_{SS}$ | L · kg$^{-1}$ | 1.11 ± 0.11 | 1.15 ± 0.07 | 1.10 ± 0.15 |

TABLE 2

Pharmacokinetic parameters of SD rats after a single oral gavage administration of A1, A3, and A6 at 10 mg/kg

| Parameters | Unite | Oral gavage | | |
|---|---|---|---|---|
| | | A1 (R = H) Mean ± SD | A3 (R = CH$_3$) Mean ± SD | A6 (R = C$_5$H$_9$) Mean ± SD |
| Doseage | mg · kg$^{-1}$ | | 10.0 | |
| K$_{el}$ | h$^{-1}$ | 0.523 ± 0.046 | 0.818 ± 0.036 | 1.77 ± 0.28 |
| t$_{1/2}$ | h | 1.34 ± 0.12 | 0.849 ± 0.055 | 0.513 ± 0.041 |
| t$_{max}$ | h | 0.500 ± 0 | 0.250 ± 0 | 0.500 ± 0 |
| C$_{max}$ | ng · mL$^{-1}$ | 3121 ± 173 | 1865 ± 251 | 259 ± 28 |
| AUC0-t | h · ng · mL$^{-1}$ | 5712 ± 802 | 2341 ± 334 | 264 ± 36 |
| AUC$_{0-inf}$ | h · ng · mL$^{-1}$ | 5744 ± 841 | 2314 ± 309 | 271 ± 43 |
| AUMC$_{0-t}$ | h · h · ng · mL$^{-1}$ | 8548 ± 240 | 2566 ± 474 | 269 ± 33 |
| AUMC$_{0-inf}$ | h · h · ng · mL$^{-1}$ | 9200 ± 336 | 2658 ± 308 | 284 ± 29 |
| MRT$_{PO}$ | h | 1.55 ± 0.20 | 1.08 ± 0.094 | 1.17 ± 0.09 |
| Vz | L · kg$^{-1}$ | 3.62 ± 0.37 | 5.22 ± 0.81 | 31.2 ± 4.8 |
| CL | mL · min · kg$^{-1}$ | 29.7 ± 3.2 | 71.3 ± 7.6 | 626 ± 93 |
| F | % | 67.1 ± 9.5 | 50.5 ± 6.8 | 13.0 ± 2.1 |

As shown in the plasma concentration versus time curves of FIG. 1 and FIG. 2 and drug pharmacokinetic parameters of Table 1 and Table 2, the exposure levels of compounds A1, A3, and A6 in SD rats (AUC$_{0-4}$) were higher. After oral gavage administration, the test compounds were detected within 15 minutes, and absorption was rapid (t$_{max}$ is only 0.25-0.5 h, reaching peak plasma concentration) and action lasted a longtime. Especially, the oral bioavailability of compound A1 was 67.5±9.5%.

The present invention synthesized a series of aza-phenalene-3-ketone derivatives. Their structures were identified by nuclear magnetic resonance spectroscopy. They were tested for PARP inhibition. Results show that the aza-phenalene-3-ketone derivatives have inhibitory activities against PARP.

What is claimed is:

1. An aza-phenalene-3-ketone having Formula (I):

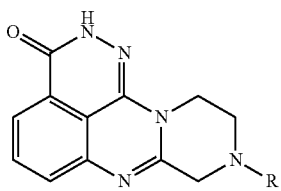

(I)

wherein R is H, methyl, ethyl, isopropyl, benzyl, or 3-methyl-3-butenyl.

2. The aza-phenalene-3-ketone of claim 1, wherein the aza-phenalene-3-ketone is selected from the group consisting of:

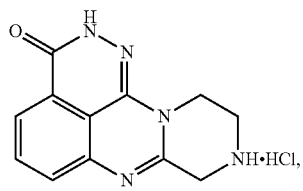

8

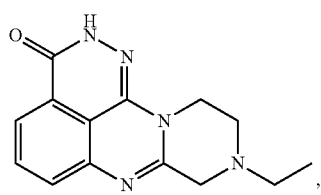

12

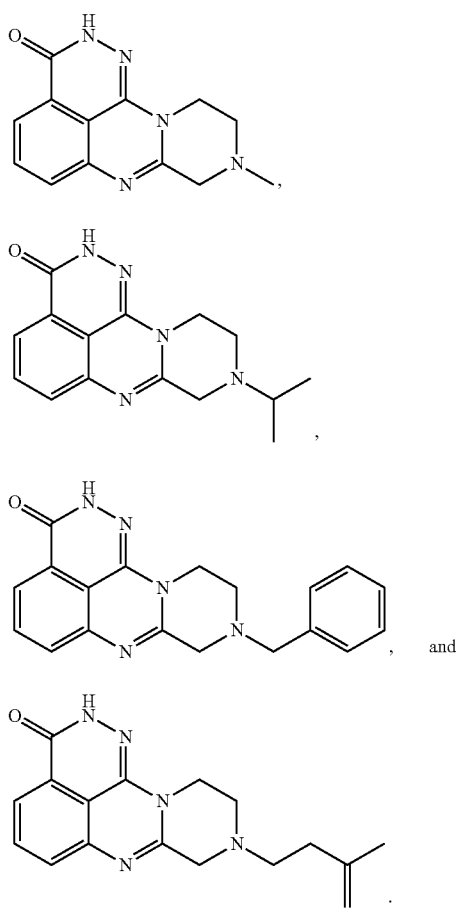
3. A method of preparing the aza-phenalene-3-ketone of claim 1, comprising:
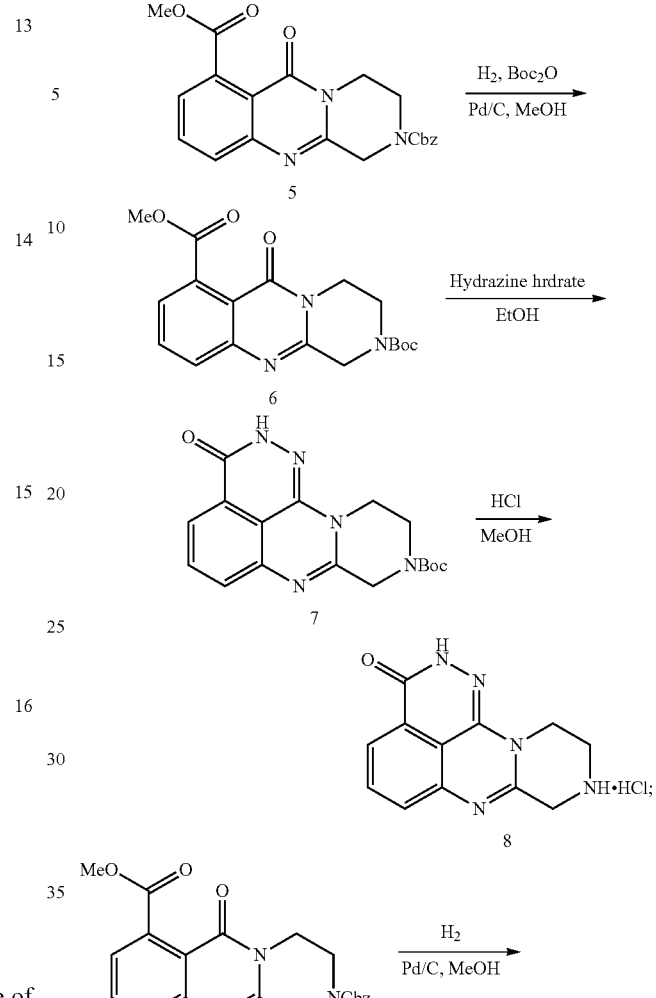
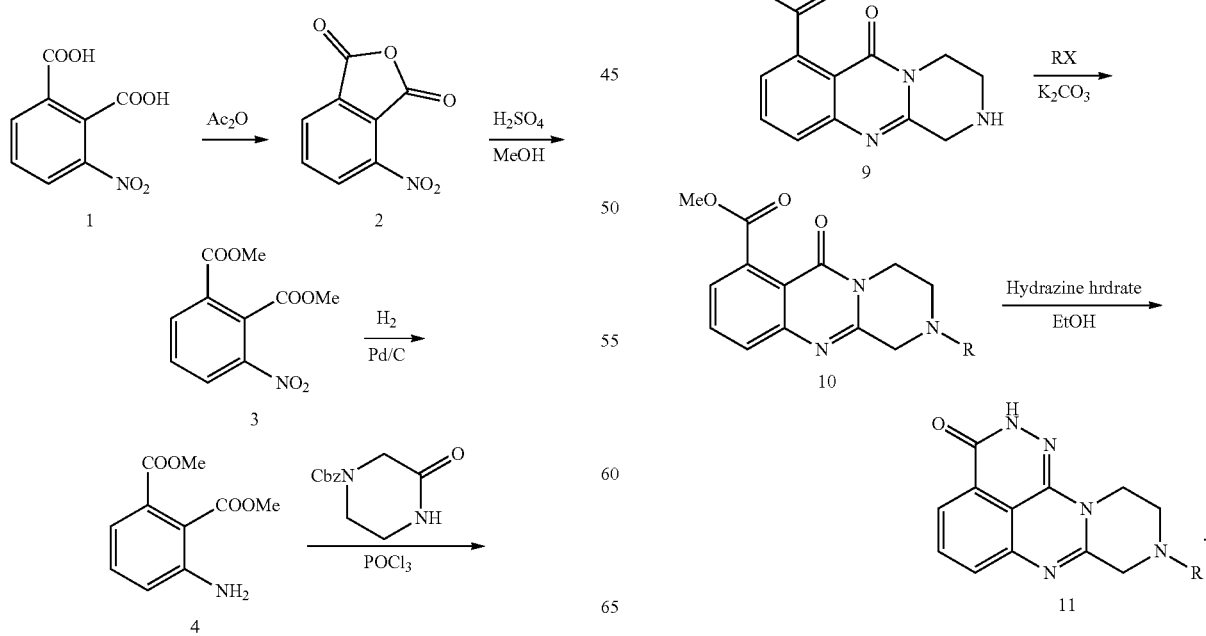

4. The method of claim 3, wherein the method comprising:
  (1) using 3-nitrophthalic acid (compound 1) as starting material, refluxing in acetic anhydride to obtain 3-nitrophthalic anhydride (compound 2);
  (2) reacting 3-nitrophthalic anhydride (compound 2) with methanol in the presence of sulfuric acid to obtain dimethyl 3-nitrophthalate (compound 3);
  (3) reducing dimethyl 3-nitrophthalate (compound 3) by catalytic hydrogenation to obtain dimethyl 3-aminophthalate (compound 4);
  (4) reacting dimethyl 3-aminophthalate (compound 4) with benzyl 3-oxopiperazine-1-carboxlyate in the presence of phosphorus oxychloride to obtain compound 5;
  (5) reducing compound 5 by catalytic hydrogenation in the presence of $Boc_2O$ to obtain compound 6; condensing compound 6 with hydrazine hydrate to obtain compound 7; removing protection group of compound 7 to obtain compound 8; and
  (6) reducing compound 5 by catalytic hydrogenation to remove protecting group Cbz to obtain compound 9, alkylating amino group of compound 9 to obtain compound 10, reacting compound 10 with hydrazine hydrate in ethanol to obtain aza-phenalene-3-ketone (compound 11).

5. A method of inhibiting PARP comprising:
providing the aza-phenalene-3-ketone of claim 1, and
contacting the aza-phenalene-3-ketone with a subject to inhibit the PARP.

\* \* \* \* \*